United States Patent [19]

Schilder et al.

[11] Patent Number: 5,795,178

[45] Date of Patent: Aug. 18, 1998

[54] PLUG FOR HEART ELECTRODE WIRE

[75] Inventors: Lothar Schilder, Hamburg; Kay Müller, Kaltenkirchen; Christian Skutta, Hamburg; Hanke Sierk, Norderstedt, all of Germany

[73] Assignee: Ethicon, Inc., Somerville, N.J.

[21] Appl. No.: 512,248

[22] Filed: Aug. 7, 1995

[30] Foreign Application Priority Data

Oct. 13, 1994 [DE] Germany .................. 44 37 818.1

[51] Int. Cl.$^6$ .................................................. H01R 4/24
[52] U.S. Cl. ........................................ 439/417; 439/725
[58] Field of Search .................................. 439/410, 411, 439/417–419, 816–823, 856, 864, 863, 787, 788, 789, 725

[56] References Cited

U.S. PATENT DOCUMENTS 1,241,627  10/1917  Hadfield ........................ 439/817
3,806,860   4/1974  Flammini ....................... 439/817
4,072,391   2/1978  Hung ............................. 439/863
4,824,406   4/1989  Vause ............................ 439/864

FOREIGN PATENT DOCUMENTS

954619  12/1956  Germany ......................... 439/817

Primary Examiner—David L. Pirlot
Attorney, Agent, or Firm—Emil Richard Skula

[57] ABSTRACT

A plug (101) for connection to the stripped end of a heart electrode wire or of another implantable wire comprises a contact piece (110), the front region of which is constructed as a plug pin (112) and the rear region (114) of which has a recess (118), an insulating housing (120) which surrounds the rear region (114) of the contact piece (110) and leaves free access to the recess (118), and a clamping piece (130) which, in the assembled state, engages with the recess (118), whereby the stripped wire end is bent round and clamped in the recess (118).

8 Claims, 13 Drawing Sheets

PLUG FOR HEART ELECTRODE WIRE

TECHNICAL FIELD

The invention relates to a plug for connection to the stripped end of a heart electrode wire or of another implantable wire for medical applications.

BACKGROUND OF THE INVENTION

A heart electrode wire or heart wire is an electrode which is secured by one end to the heart wall in a surgical operation by means of a surgical needle and then fed through the thorax to the outside. There the needle is removed so that a plug can be attached to the free wire end, which is already stripped or which must be stripped. The plug serves for connection to an external heart pacemaker or an ECG monitor in order to stimulate or observe the heart's activity when needed.

Known from DE 34 45 102 C1 is a plug for connection to the stripped end of a heart electrode wire. An electrically conductive plug pin is provided with a recess running transversely to its longitudinal extension, into which the stripped wire end is threaded. Part of the plug pin is surrounded by a displaceable collet made from insulating material, which is shorter than the plug pin. To thread the stripped wire end in, the collet is moved such that the recess lies free. The collet is then pushed into the use position where it clamps in the wire end and exposes the plug-in end of the plug pin. A disadvantage of the previously known plug is its troublesome handling.

SUMMARY OF THE INVENTION

It is the object of the invention to provide a plug for connection to the stripped end of a heart electrode wire or of another implantable wire, which can be secured to a stripped wire end in quick and simple manner and which then has a mechanically secure seat and provides a good electrical contact.

This object is achieved by a plug having the features of claim 1. Advantageous embodiments emerge from the dependent claims. The plug according to the invention for connection to the stripped end of a heart electrode wire or of another implantable wire has a contact piece, the front region of which is constructed as a plug pin. The rear region of the contact piece has a recess. An insulating housing surrounds the rear region of the contact piece, leaving free access to the recess. In the assembled state (i.e. when the plug is connected to the wire) a clamping piece, which is preferably made exclusively from insulating material, engages with the recess. In this state the stripped wire end is bent round and clamped in the recess, as a result of which a mechanically secure seat is achieved on the one hand and a good electrical contact on the other.

In a preferred embodiment the recess runs in the direction of the longitudinal axis of the plug and is accessible from the rear end of the contact piece. The recess is preferably cylindrical. The clamping piece is provided with a transversely-running through bore through which the stripped wire end is fed on assembling the plug. The clamping piece is then inserted into the recess. As a result the stripped wire end bends round, which ensures a good mechanical attachment and a safe electrical contact.

In another embodiment the recess is arranged laterally at the contact piece and is accessible via a longitudinal groove provided laterally at the insulating housing which extends as far as the rear end of the insulating housing. The clamping piece can be constructed as a cover for the insulating housing. To assemble, the stripped wire end is introduced into the longitudinal groove from behind. The clamping piece is then inserted, whereby it at least partially covers the longitudinal groove and engages with a peg in the recess. The peg presses part of the stripped wire end into the recess, as a result of which it is bent round and clamped in secure manner. The longitudinal groove can be provided with a relatively large cross-section, which makes the introduction of the stripped wire end into the rear end of the plug considerably easier and thus permits a particularly quick handling. Locking elements can ensure a secure seat of the clamping piece. The clamping piece can be constructed as a separate part which can be pushed laterally onto the insulating housing. In this case it is particularly advantageous if it is initially held by means of locking elements in a pre-assembled state, in which it is locked in an intermediate position at the insulating housing and in so doing still leaves free the rear end of the longitudinal groove. After introducing the stripped wire end, the clamping piece is pressed into its final position, i.e. the assembled state. Alternatively, the clamping piece can be constructed as one piece with the insulating housing and can be hinged about a film hinge for attaching the stripped wire end.

When the plug is not connected to an external heart pace maker or to an ECG monitor, contact with the plug pin should be avoided. In fact, electrical charges can be transferred by a contact, e.g. by nursing staff, which can lead to an undesired, and, in unfavourable circumstances, life-threatening stimulation of the heart. In order to prevent this an insulating cap can be provided on the plug according to the invention to cover the plug pin. In preferred embodiments, this is not a separate component, but a movable or displaceable constituent of the complete plug which exposes the plug pin when necessary. The insulating cap can thus be constructed as a sleeve which, in the insulating state, surrounds the front region of the plug pin and which can be moved back into an insulating intermediate housing arranged around the rear region of the plug pin, or can alternatively be moved on an insulating guide arranged around the rear region of the plug pin. Rearwards movement preferably takes place against the force of a spring so that the insulating cap automatically covers the plug pin when it is not inserted into a socket. The insulating cap can also be constructed as an insulating bellows. Another variant, which has the same effect as an insulating cap, is a helical spring made from insulating material which is secured in the rear region of the plug pin and surrounds the plug pin. In order to expose the front region of the plug pin, it can be pushed back against its spring tension.

The invention is described in more detail below with reference to several embodiments. The drawings show:

DESCRIPTION OF THE PREFERRED EMBODIMENT

Figure 1:
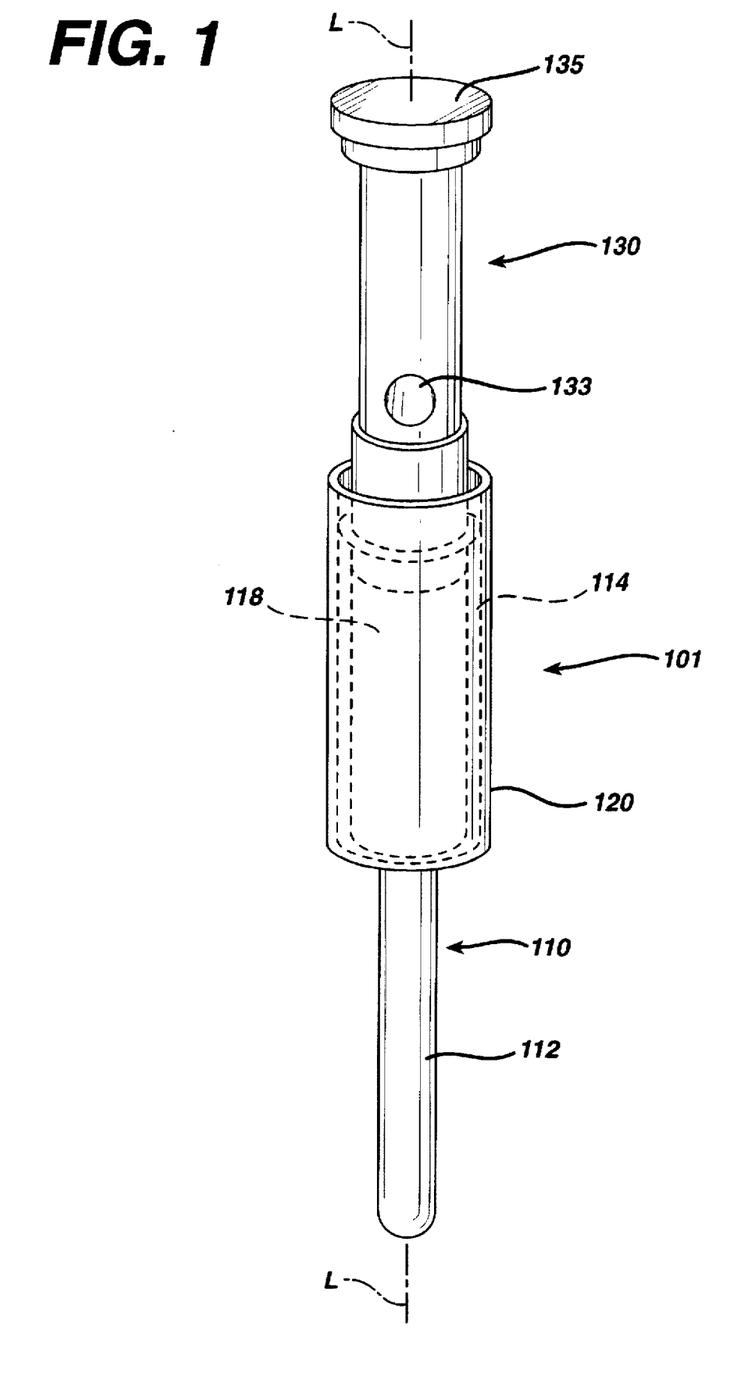
FIG. 1 a perspective overall view of a first embodiment of the plug according to the invention, FIG. 2 two longitudinal sections of the plug according to the first embodiment, in part (a) during assembly and in part (b) in the ready assembled state, FIG. 3 an insulating cap, pre-tensioned by a spring, for covering the plug pin, FIG. 4 an exploded view of a variant of the first embodiment in which an insulating cap according to FIG. 3 is provided, FIG. 5 an exploded view of a second embodiment of the plug according to the invention, FIG. 6 a perspective view of the plug according to FIG. 5, FIG. 7 an illustration of the action principle of the plug according to the second embodiment, in part (a) a longitudinal section during assembly and in part (b) a longitudinal section in the ready assembled state, FIG. 8 an exploded view of a third embodiment of the plug according to the invention, FIG. 9 a perspective view of the plug according to FIG. 8 prior to assembly, FIG. 10 in parts (a), (b), (c) and (d) show successive phases during assembly of the plug according to the third embodiment in schematic longitudinal section representation, FIG. 11 partial views of a fourth embodiment of the plug according to the invention in longitudinal section, in part (a) prior to assembly and in part (b) in the ready assembled state, FIG. 12 a partial view of a fifth embodiment of the plug according to the invention in longitudinal section, FIG. 13 a sectional representation, unrolled into the plane of the paper, of the cylinder lateral area, with the longitudinal axis X—X from FIG. 12, running through the axis Y—Y from FIG. 12, in the assembled state, FIG. 14 a second embodiment of the insulating cap in longitudinal section, FIG. 15 a third embodiment of the insulating cap in schematic longitudinal section, FIG. 16 a fourth embodiment of the insulating cap in longitudinal section, and FIG. 17 a fifth embodiment for a device for contact protection of the plug pin, in which a helical spring made from insulating material is used instead of an insulating cap.

Shown in FIGS. 1 and 2 is a first embodiment of a plug 101 for connection to the stripped end 102 of a heart electrode wire or of another implantable wire. The essential components of the plug 101 are a contact piece 110 made from metal, an insulating housing 120 and a clamping piece 130.

As FIG. 2 in particular shows, the front region of the contact piece 110 is constructed as a plug pin 112. The plug pin 112 fits into the socket of an allotted device or of an extension lead. The rear region 114 of the contact piece 110 is constructed as a hollow cylinder, which stands open at its rear side, having a bottom piece or transition region 115, from which the plug pin 112 extends, and a wall 116. The inside of the hollow cylinder is called a recess 118 in the following. It runs in the direction of the longitudinal axis L—L of the plug 101 and is accessible from the rear end of the contact piece 110.

The contact piece 110 is surrounded in its rear region 114 by the insulating housing 120 made from plastic. At its rear end 121 the insulating housing 120 projects beyond the rear end of the contact piece 110. The front side 122 of the insulating housing 120 is provided with an opening through which the plug pin 112 is introduced. The insulating housing 120 leaves free access to the recess 118. The connection to the contact piece 110 is effected by sticking or clamping.

The clamping piece 130 consists of insulating plastic and is essentially rotationally symmetrical relative to the longitudinal axis L—L. The diameter of its front end region 131 corresponds to the internal diameter of the recess 118, so that, upon pressing in into the recess 118, the clamping piece 130 is guided by its front end region 131. The middle region 132 of the clamping piece 130 has a somewhat smaller diameter. In this zone a through bore 133 runs transversely through the clamping piece 130. Constructed in the rear end region of the clamping piece 130 are a stepped section 134 and a widened-end section 135. If the clamping piece 130 is fully introduced into the recess 118, which is the case in the assembled state of the plug, it essentially fills the recess 118, see FIG. 2(b). The stepped section 134 lies in the rear end region of the insulating housing 120, whilst the widened-end section 135 covers the rear end of the insulating housing 120 and therefore also of the contact piece 110.

Figure 2A:
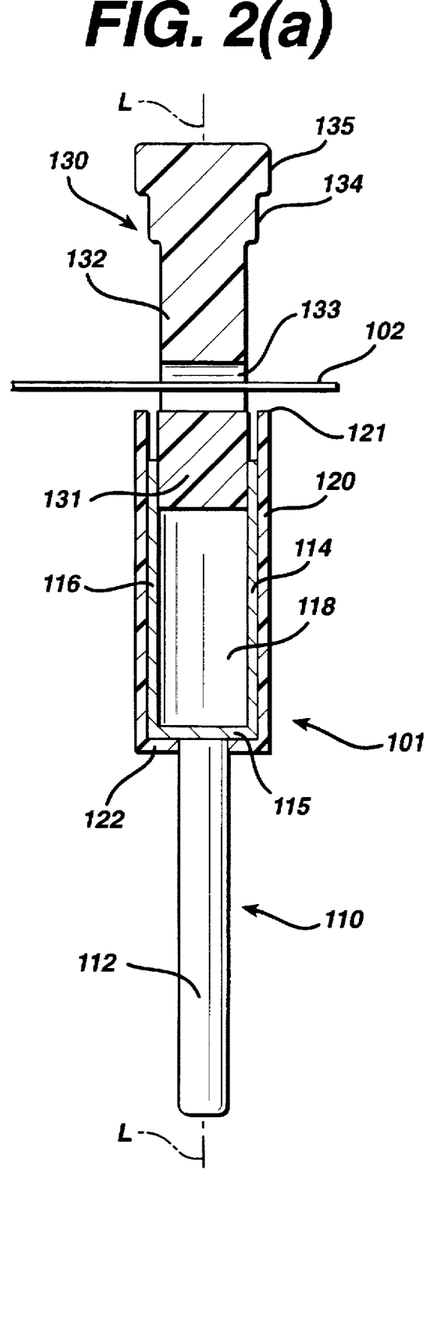
Figure 2B:
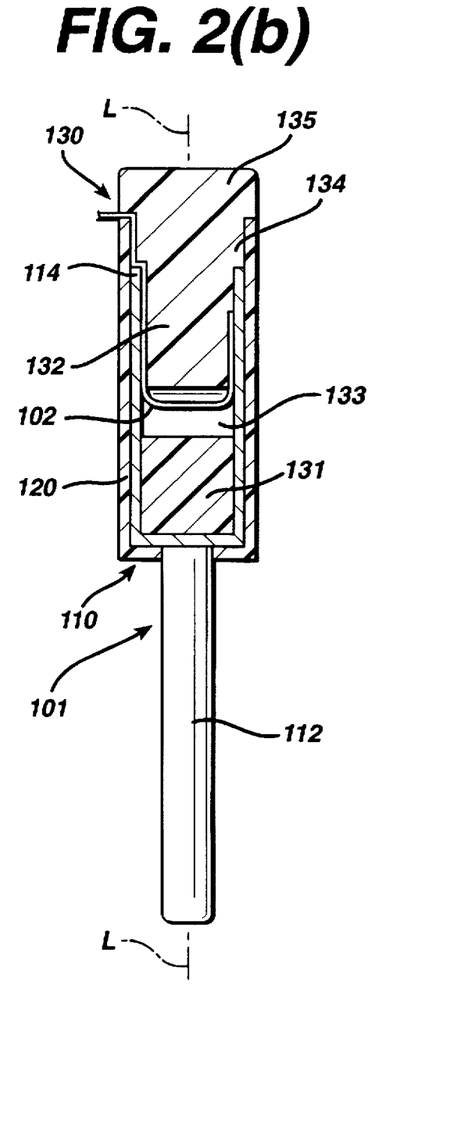

How the stripped wire end 102 is attached to the plug 101 is shown in FIGS. 2(a) and (b). In the state shown in FIG. 2(a), the clamping piece 130 is introduced a slight distance into the recess 118. The plug 101 can be supplied pre-assembled in this position. The through bore 133 is still freely accessible. During assembly, the stripped wire end 102 is pushed from one side (in FIG. 2(a) from the left) through the through bore 133. The clamping piece 130 is then pushed forwards, i.e. in the direction of the plug pin 112, until the widened-end section 135 lies against the rear end 121 of the insulating housing 120. The stripped wire end 102 bends, see FIG. 2(b), so that a firm mechanical seat is ensured on the one hand and a good electrical contact with the rear region 114 of the metallic contact piece 110 on the other. Since the clamping piece 130 has a slightly smaller diameter in its middle region 132, there is sufficient space for the stripped wire end 102.

If the plug 101 is ready assembled, the wire should not project from the rear end region of the plug 101 without insulation. This can be achieved by inserting the end of the wire insulation up to the inside of the plug 101 during assembly. If the wire insulation is substantially thicker than the stripped wire end 102, it is advantageous to provide a channel in the rear end region of the clamping piece 130 to accommodate the wire section which is thicker due to the wire insulation.

Figure 3:
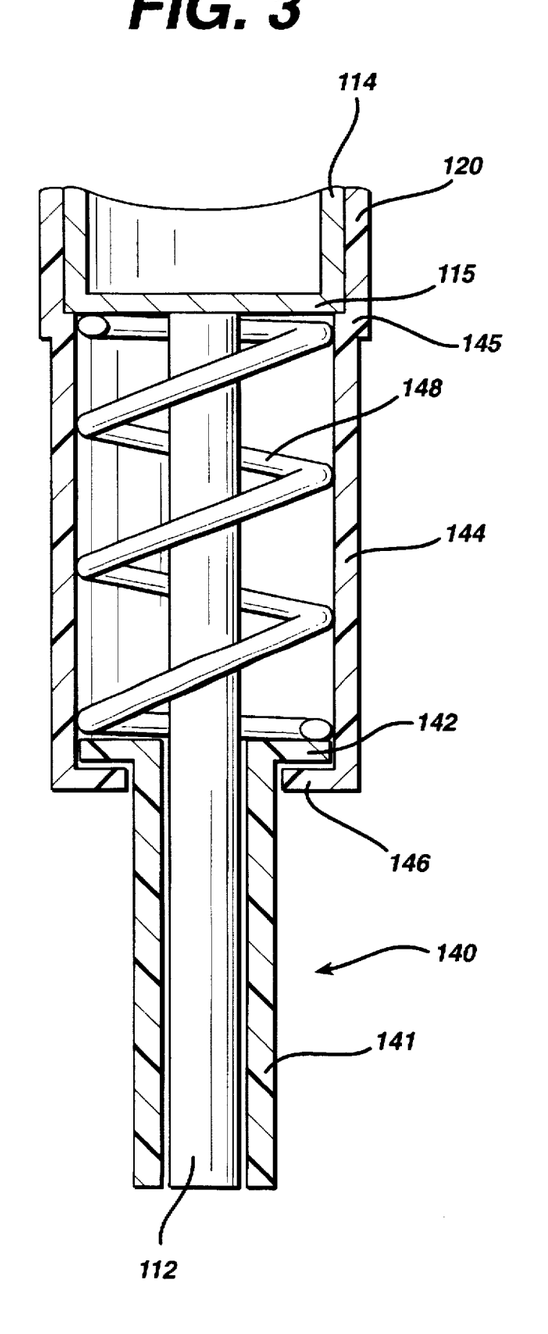

FIG. 3 shows an insulating cap 140, which in a preferred embodiment covers the plug pin 112, if it is not inserted into a socket. The insulating cap 140 consists of a sleeve 141 made from plastic, the rear end of which is widened to give a flange 142. In order to expose the plug pin 112, the insulating cap 140 can be moved back into an insulating intermediate housing 144. In the embodiment shown in FIG. 3, the insulating intermediate housing 144 is constructed as one piece with the insulating housing 120, whereby the transition takes place at a stepped section 145. The stepped section 145 serves as a stop limit for the transition region 115 of the contact piece 110 which is constructed according to FIGS. 1 and 2. The insulating intermediate housing 144 has a front face 146 with an opening for the sleeve 141. The insulating cap 140 is pre-tensioned by a helical spring 148, which lies between the transition region 115 and the flange 142, in such a way that the plug pin 112 is covered. When the plug is introduced into a socket, some force must be expended in order to compress the helical spring 148. On removal from the socket the helical spring 148 pushes the insulating cap 140 over the plug pin 112 again, so that a reliable protection against undesired contact is achieved.

Figure 4:
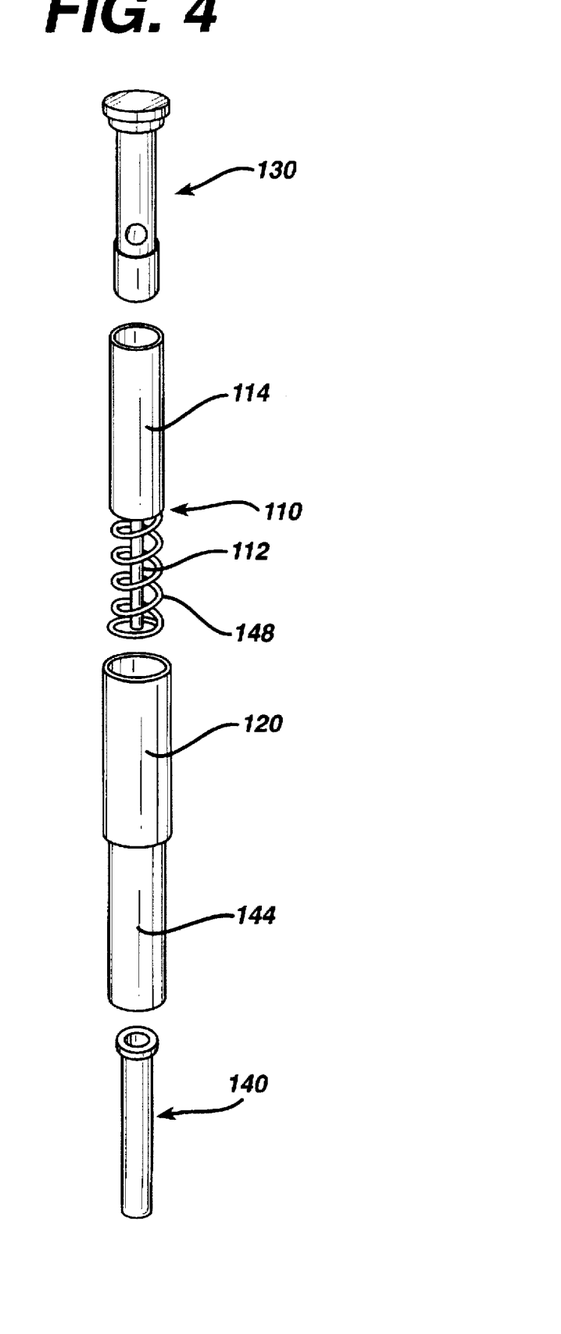

FIG. 4 shows the version of the plug according to FIGS. 1 and 2, supplemented by the insulating cap according to FIG. 3 in exploded view. During pre-assembly, which is to be carried out in factory, the insulating cap 140 is firstly inserted from the rear end of the insulating housing 120. The contact piece 110 is then inserted with fitted helical spring 148 and clamped in the insulating housing 120. Finally, the clamping piece 130 can be brought into the position shown in FIG. 2(a).

Figure 5:
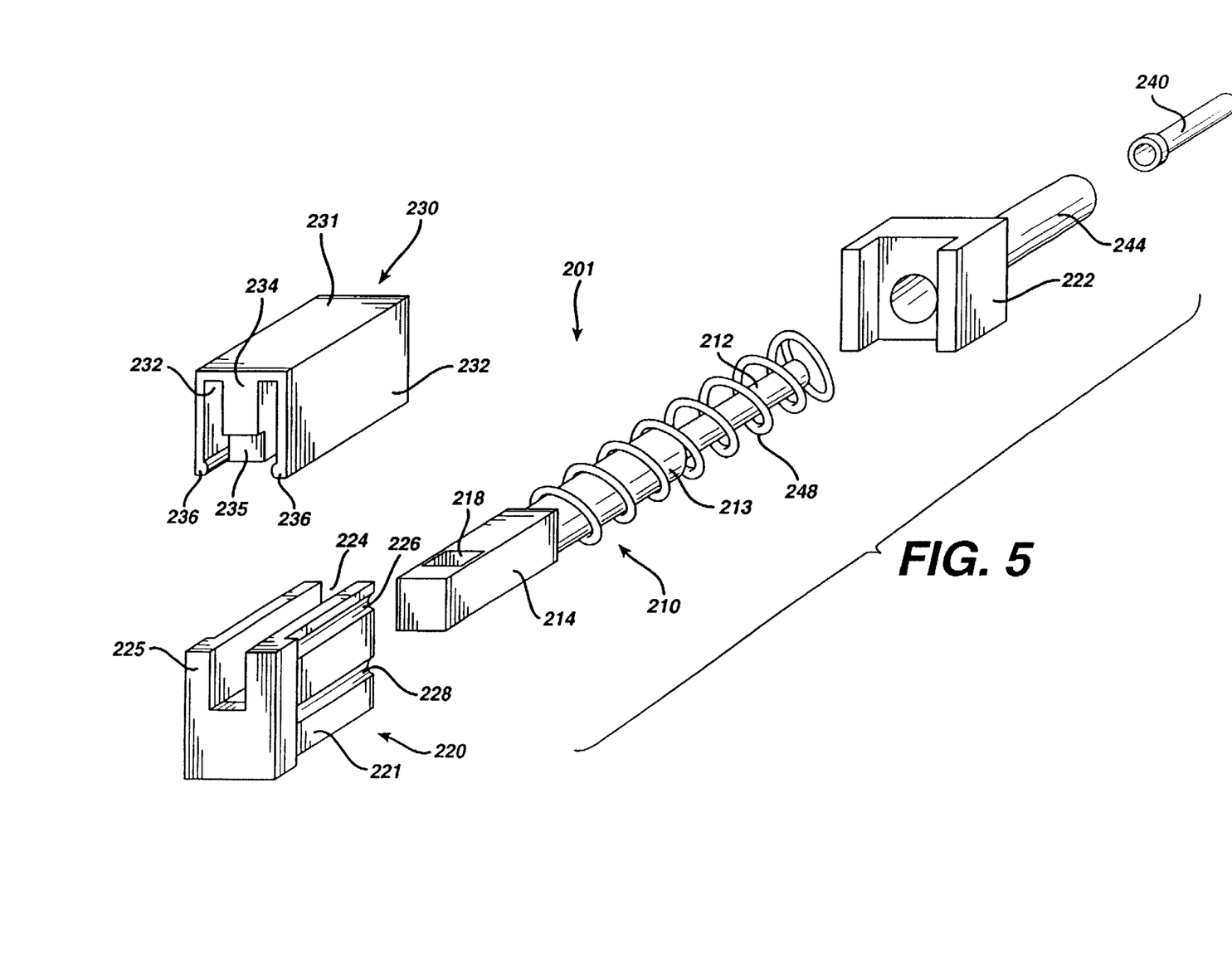
Figure 6:
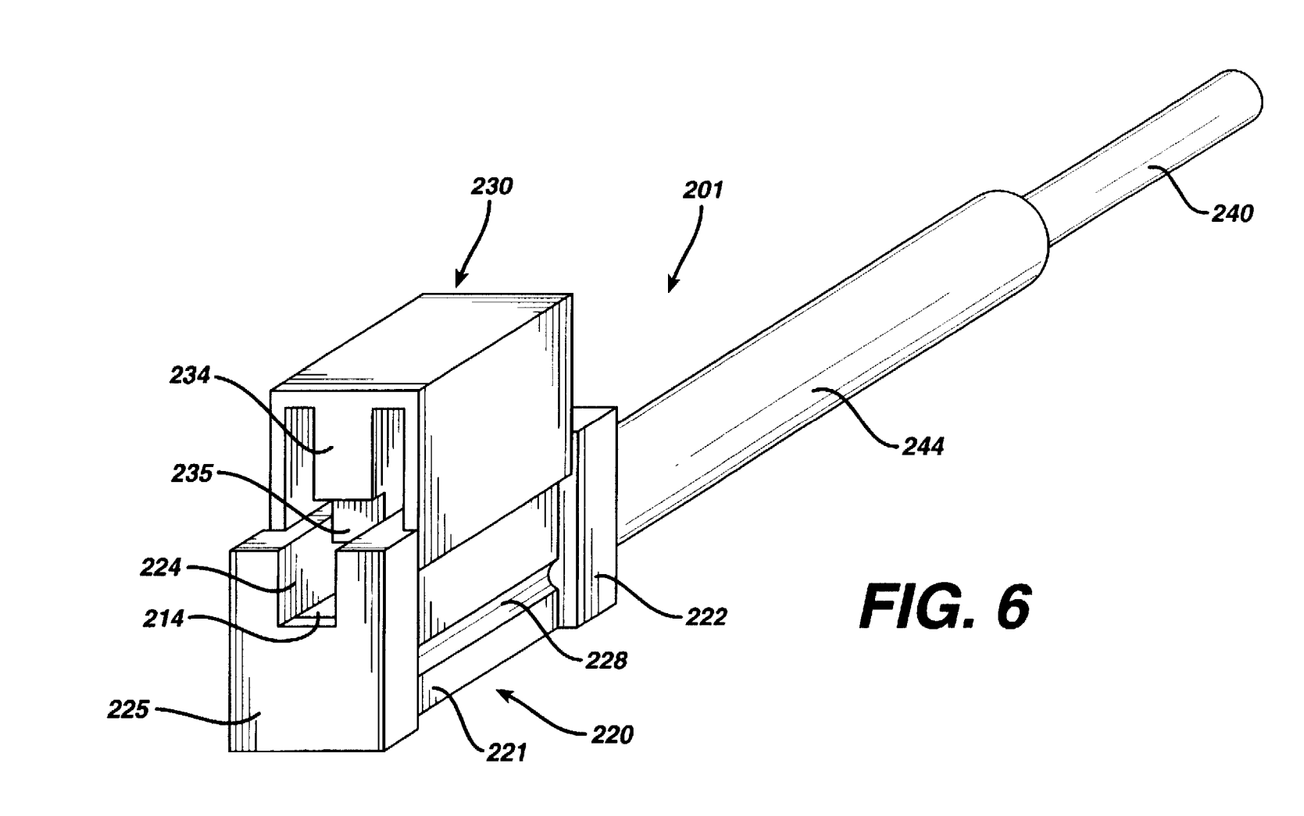
Figure 7A:
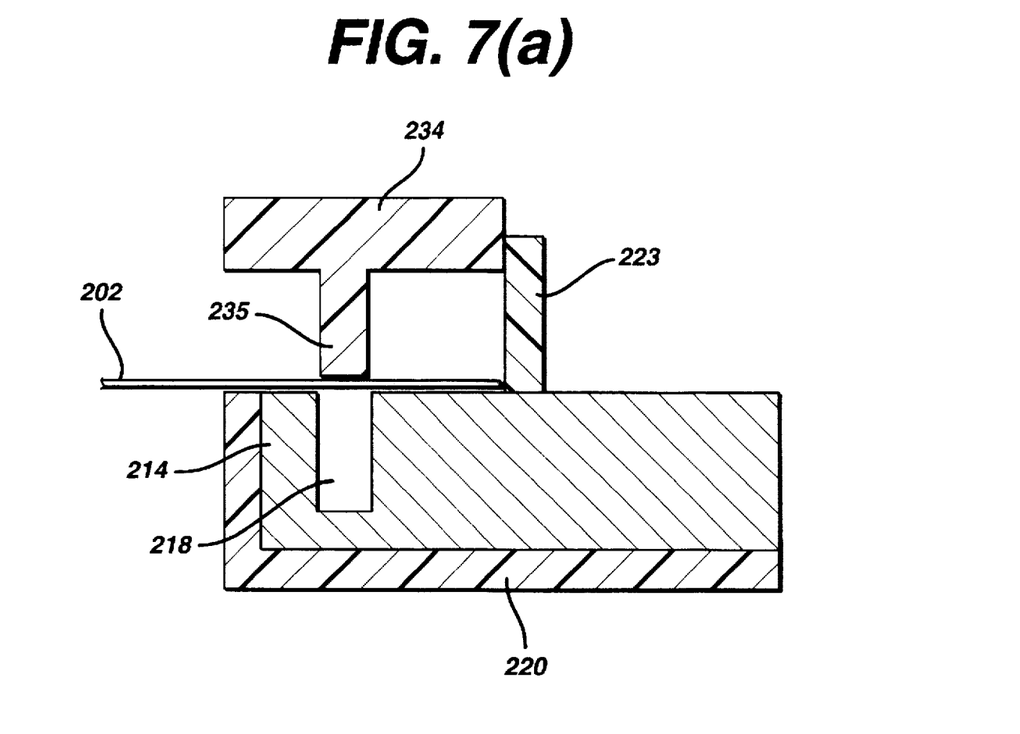
Figure 7B:
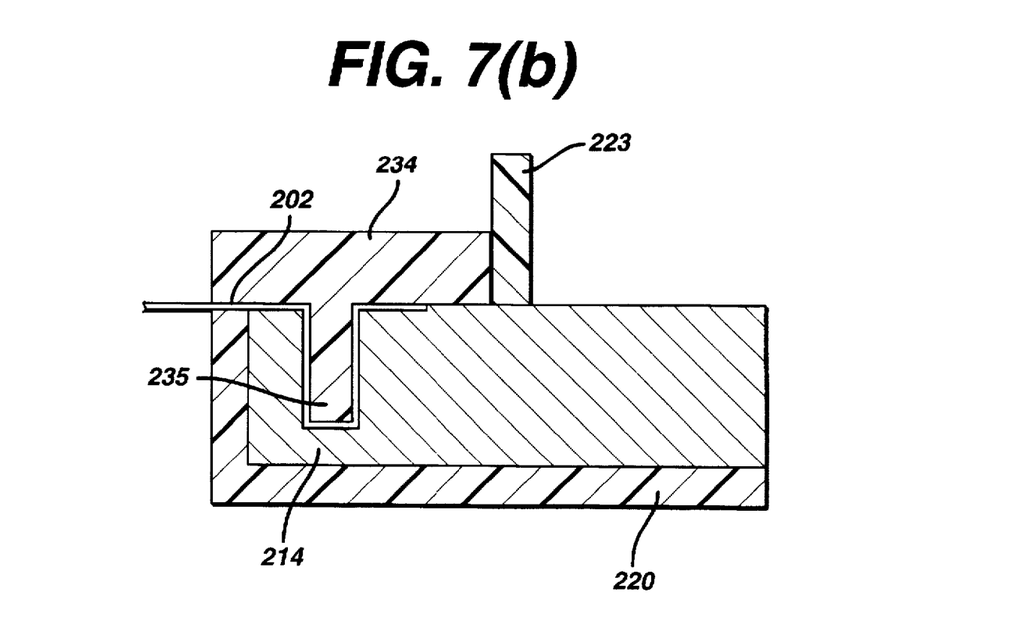

FIGS. 6 and 7 show a second embodiment of a plug 201 according to the invention, FIG. 5 in exploded view and FIG. 6 in the pre-assembled state prior to the insertion of a stripped wire end. How the stripped wire end 202 is clamped is shown schematically in FIG. 7.

The plug 201 again has a contact piece 210, an insulating housing 220 and a clamping piece 230 and an insulating cap 240. The front region of the contact piece 210 is constructed as a plug pin 212 with circular cross-section. Joined to this is a middle region 213 which has a larger diameter. The rear region 214 of the contact piece 210 has a rectangular cross-section, as a result of which it is secured against twisting within the insulating housing 220. Provided laterally at the rear region 214 of the contact piece 210 is a recess 218 which has a rectangular cross-section in the embodiment.

The insulating housing 220 is constructed as two parts and consists of a rear part 221 and a front part 222. The front part 222 is joined as one piece to an insulating intermediate housing 244 which surrounds the middle region 213 of the contact piece 210 and serves to accommodate the insulating cap 240 when this is pushed backwards against the force of a helical spring 248, in order to expose the plug pin 212. The insulating cap 240 is designed and arranged in similar manner to the embodiment shown in FIG. 3.

In order to assemble the plug 201 in factory, the insulating cap 240 is firstly inserted from behind into the front part 222 of the insulating housing and the insulating intermediate housing 244, then the contact piece 210 consisting of metal is pushed in with the helical spring 248 and, finally, the rear part 221 of the insulating housing 220 is pushed onto the rear region 214 of the contact piece 210 which is then projecting from the front part 222 of the insulating housing 220. The rear part 221 and the front part 222 of the insulating housing 220 can be stuck or clamped to one another.

The recess 218 in the contact piece 210 is accessible via a longitudinal groove 224, arranged laterally at the insulating housing 220, which extends as far as the rear end 225 of the insulating housing 220. Provided at the sides of the rear part 221 of the insulating housing 220 are upper locking recesses 226 and lower locking recesses 228, see FIG. 5.

The clamping piece 230 consists of a connecting wall 231 to which on both sides side walls 232 running parallel to one another connect. Between the side walls 232, starting from the connecting wall 231, there is an essentially rectangular pressure part 234, which is provided with a peg 235, which is matched to the cross-section of the recess 218. Arranged in the region of their free ends on the insides of the side walls 232 are stop projections 236.

In the pre-assembled state, which is shown in FIG. 6, the stop projections 236 lie in the upper locking recesses 226. The lower end of the peg 235 does not yet project into the recess 218, with the result that the stripped wire end 202 can be introduced comfortably into the longitudinal groove 224 which is accessible from the rear end 225 of the insulating housing 220, see FIG. 7 (a). On introducing the stripped wire end 202, the front part 222 of the insulating housing 220 forms a limiting means as a stop limit 223. For the final assembly of the plug 201, the clamping piece 230 is pressed downwards until the stop projections 236 lock in the lower stop recesses 228, see also FIG. 7(b). The pressure part 234 now essentially fills the cross-section of the longitudinal groove 224. The peg 235 also projects into the recess 218, so that the stripped wire end 202 is bent round and clamped. This produces a reliable mechanical attachment and a good electrical contact. When attaching the plug 201 to the stripped wire end 202, care should again be taken that no bare wire region is exposed subsequently.

Figure 8:
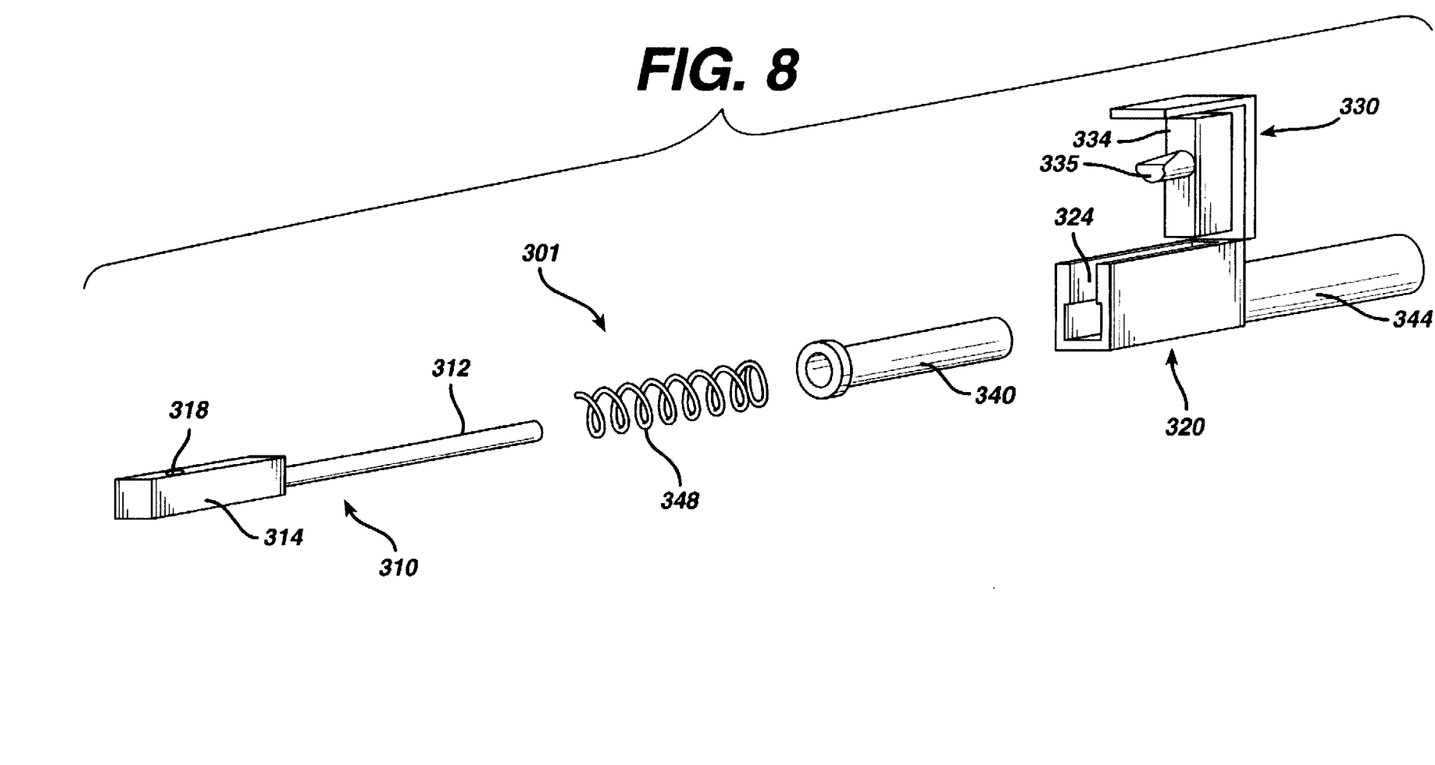

A third embodiment of a plug 301 according to the invention is constructed in a similar manner to the second embodiment. FIG. 8 shows an exploded view and FIG. 9 the plug 301 in assembled state before the stripped wire end is attached. Shown in FIG. 10, part (a) to part (d), are successive phases during the clamping of the stripped wire end 302.

As can be seen from FIG. 8, the plug 301 again has a contact piece 310, an insulating housing 320 and a clamping piece 330 which is this time constructed as one piece with the insulating housing 320. An insulating cap 340 serves to cover the plug pin, which, in a similar manner as described in the preceding embodiments, can be pushed back against the force of a helical spring 348 into an insulating intermediate housing 344, which is moulded onto the insulating housing 320, in order to expose the plug pin.

FIG. 8 illustrates how the plug 301 can be assembled in factory by pushing in the insulating cap 340, the helical spring 348 and the contact piece 310 over the rear end of the insulating housing 320. The contact piece 310 can be clamped or stuck in the insulating housing 320.

A plug pin 312 again forms the front region of the contact piece 310, whilst the rear region 314 has a rectangular cross-section in order to prevent twisting within the insulating housing 320. Provided laterally is a recess 318 in the form of a cylindrical bore. The contact piece 310 consists of metal.

The insulating housing 320 has two side walls 322 running parallel to one another, the wall thickness of which is smaller in the lower region than in the upper region. As a result, two projections 323 are formed against which, in the pre-assembled state (see FIG. 9), the rear region 314 of the contact piece 310 rests, so that the contact piece 310 cannot slip upwards. The upper side of the rear region 314 of the contact piece 310 and thus the recess 318 are accessible via a longitudinal groove 324 formed between the side walls 322. Towards the rear end 325 of the insulating housing 320 the longitudinal groove stands open, whilst at its front end it is closed by a transverse wall 327 connecting the two side walls 322.

The clamping piece 330 is hinged to the transverse wall 327 by means of a film hinge 337. In the assembled state, see FIG. 10 (d), a connecting wall 331 forms a cover for the longitudinal groove 324. From the rear end of the connecting wall 331 there projects a wall section 333 which, in the assembled state, covers the rear face of the insulating housing 320 and thus the longitudinal groove 324 from behind. The cross-section of the longitudinal groove 324 above the rear region 314 of the contact piece 310 is essentially filled in the assembled state by a pressure part 334 which is arranged on the under side of the connecting wall 331 and from which a peg 335 projects downwards.

The peg 335 serves to clamp the stripped wire end 302, as shown in FIG. 10.

Figure 9:
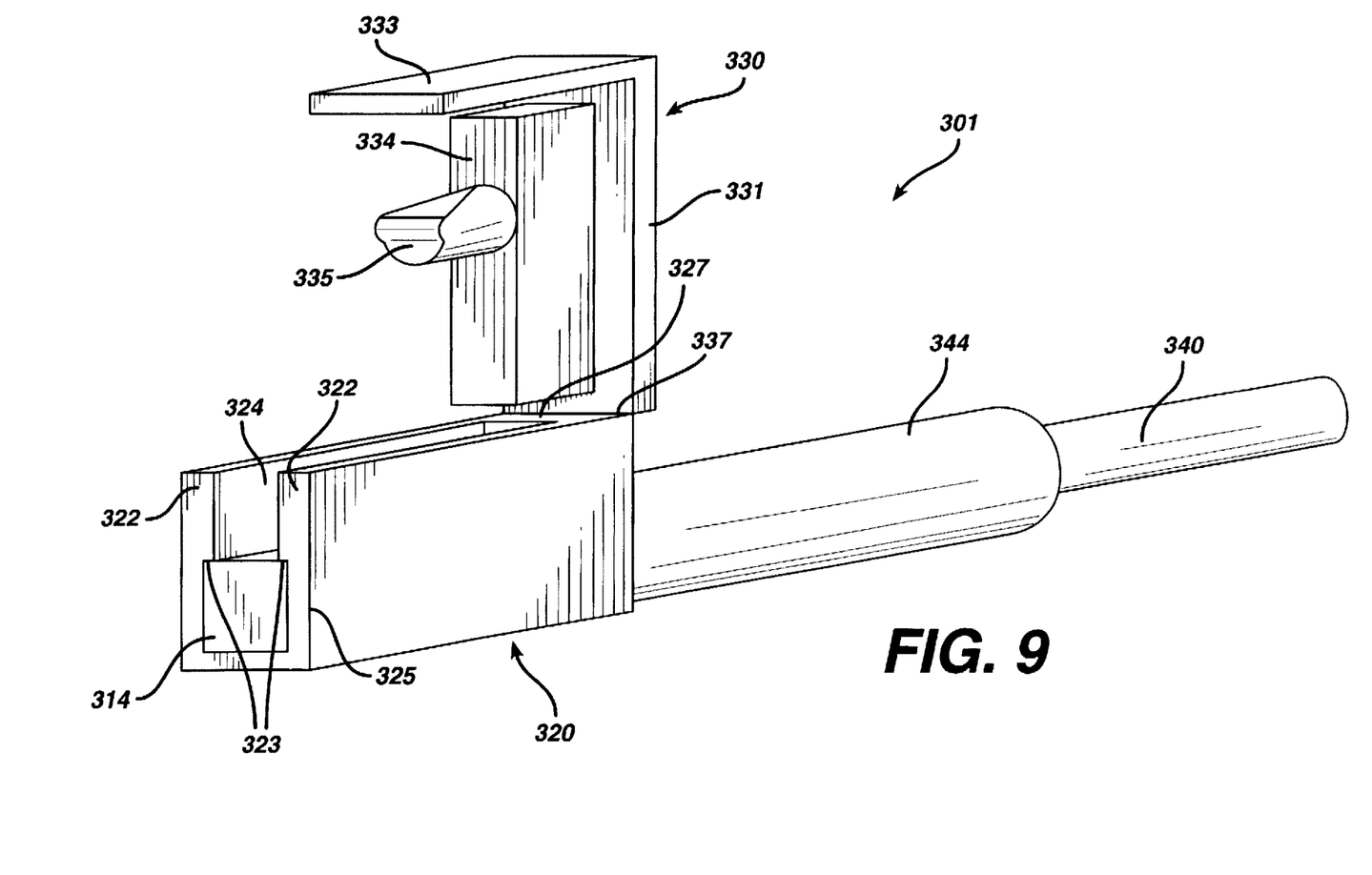
Figure 10A:
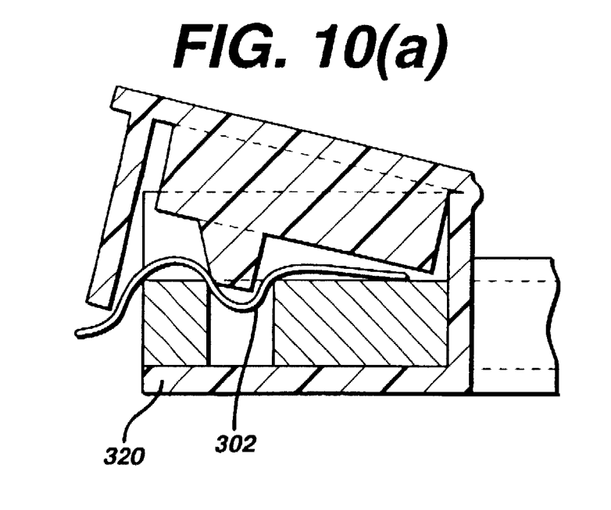
Figure 10B:
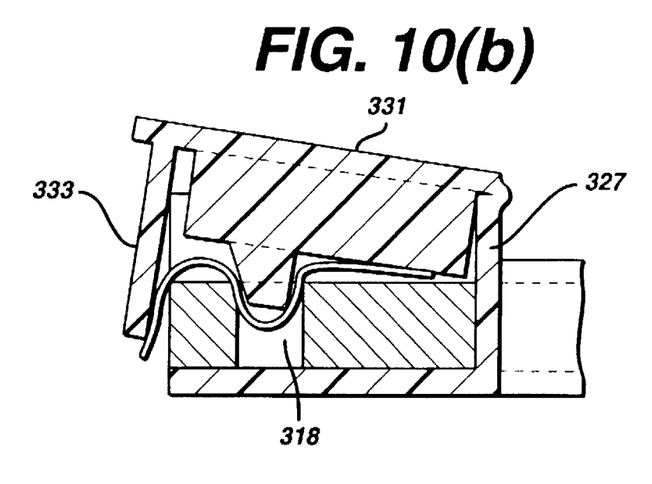
Figure 10C:
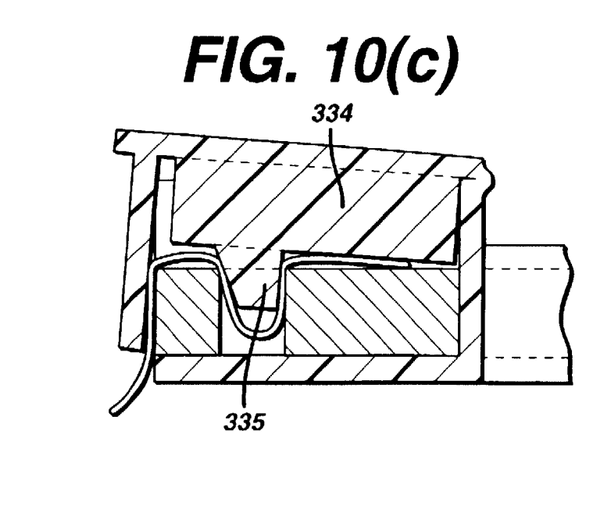
Figure 10D:
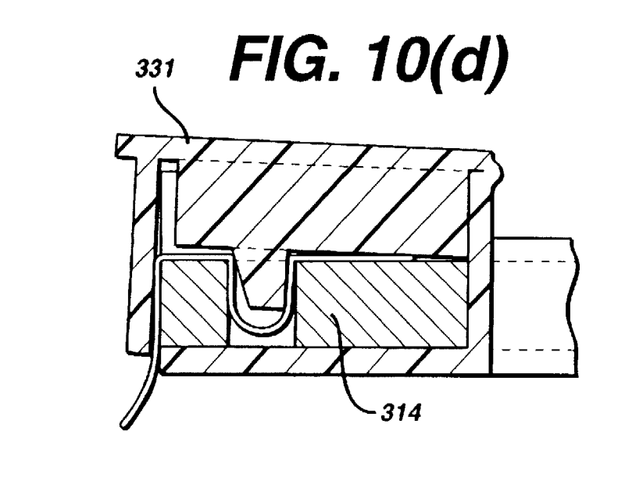

This embodiment proves to be particularly advantageous in practice. The insulating housing 320, the clamping piece 330 and the insulating intermediate housing 344 consist of one component, as a result of which the manufacturing costs are low. On-site pre-assembly is simple since the contact piece 310 and the insulating cap 340 and the helical spring 348 can be pushed in via the open rear end of the insulating housing 320. Finally, the plug 301 can be attached quickly and securely to the stripped wire end 302 because the longitudinal groove 324 is easily accessible from above and behind, provided the clamping piece 330 is raised, as shown in FIG. 9, and because the wire end 302, after insertion into the longitudinal groove 324, can be clamped using the pressure of a single finger. The insulating housing 320 is closed on all sides in the assembled state, even at the rear end 325 because of the wall section 333. Handling is also made easier because the clamping piece 330 cannot become lost in view of the fact it is formed as one piece with the insulating housing 320.

Figure 11A:
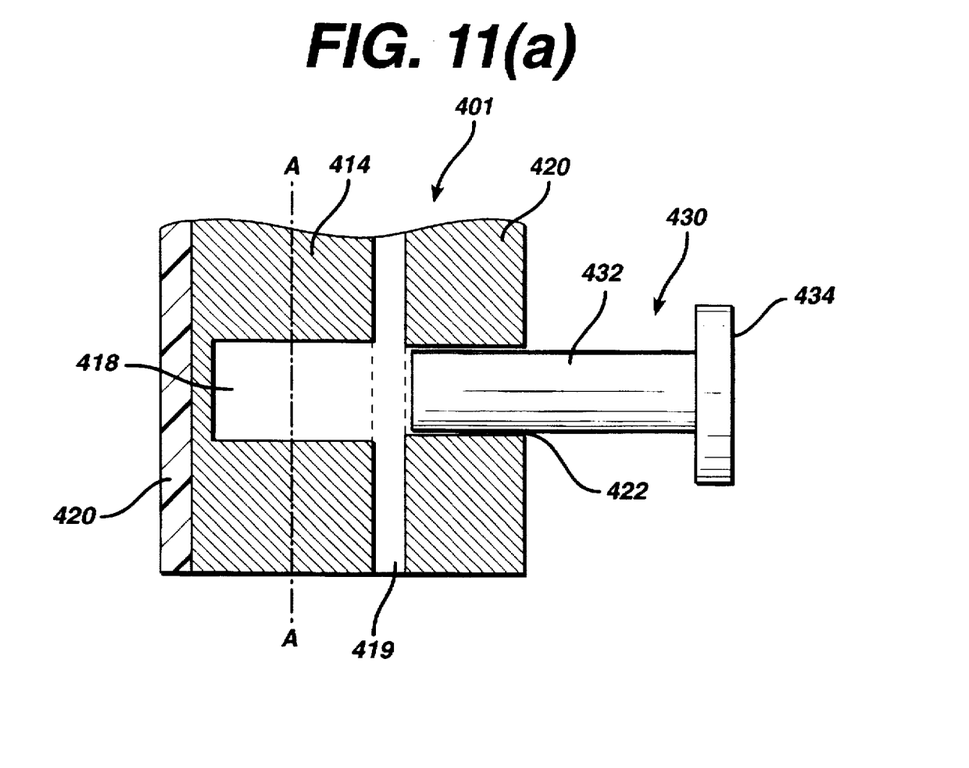
Figure 11B:
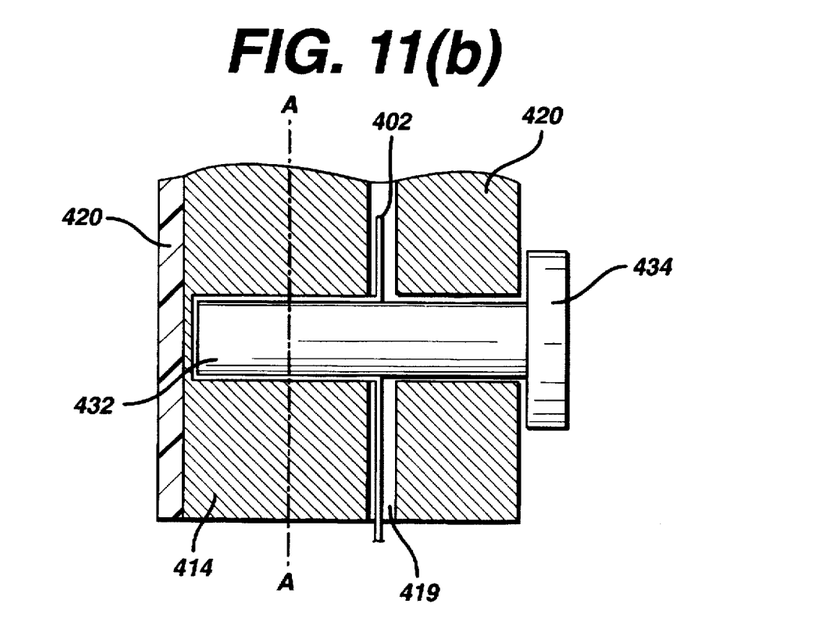

A fourth embodiment of a plug 401 according to the invention is illustrated in FIG. 11. FIG. 11 (a) shows the pre-assembled state in which the plug 401 can be supplied from factory and FIG. 11(b) the ready assembled state in which the stripped wire end 402 is clamped. It is only the rear region of the plug 401 which is shown in each case; the plug pin which is not shown is situated above FIG. 11(a) or (b).

The rear region 414 of the contact piece has a recess 418 running transversely to the plug axis A—A which, in the embodiment, is a cylindrical bore. A longitudinal channel 419, which is accessible from the rear end of the plug 401 (thus in FIGS. 11(a) and (b) from below), runs parallel to the plug axis A—A. The longitudinal channel 419 crosses the recess 418 or cuts it.

The rear region 414 of the contact piece is surrounded laterally by an insulating housing 420 which has an opening 422 over the recess 418. In the embodiment the opening 422 is circular and has a slightly smaller diameter than the recess 418. The longitudinal channel 419 can be completely or partially hollowed out from the material of the contact piece or from the material of the insulating housing 420.

Serving as a clamping piece 430 is a pin which consists of a shaft 432 and a head 434. The diameter of the shaft 432 is matched to that of the opening 422 in order to achieve a secure seat in the assembled state.

For attaching the stripped wire end 402 to the plug 401, if the plug 401 is in the pre-assembled state according to FIG. 11 (a) or if the clamping piece 430 is completely taken away, the stripped wire end 402 is introduced into the longitudinal groove 419 from behind (i.e. according to FIG. 11 from below). The clamping piece 430 can then be pressed completely into the recess 418. The stripped wire end 402 thus bends round, see FIG. 11 (b). This provides a secure mechanical hold and a good electrical contact. Because the inside diameter of the recess 418 is slightly larger than the outer diameter of the shaft 432, there is sufficient space for the stripped wire end 402.

Figure 12:
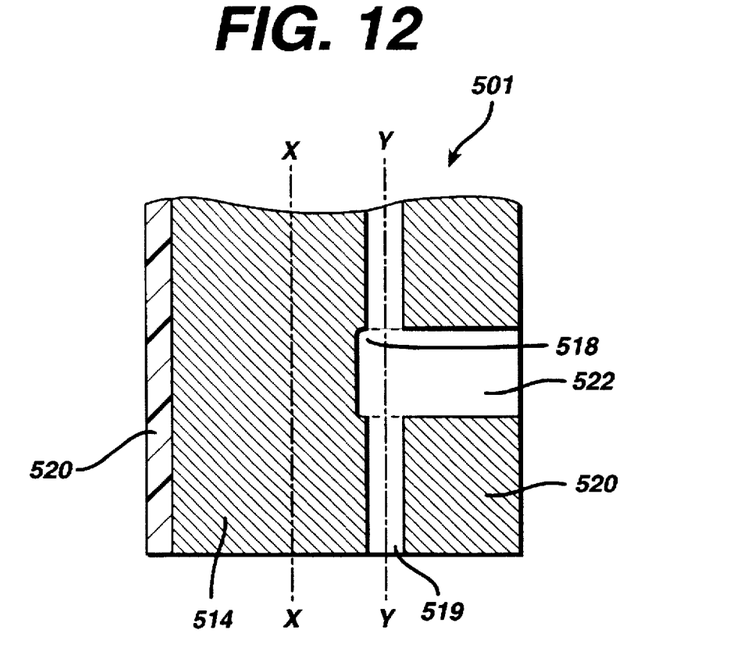
Figure 13:
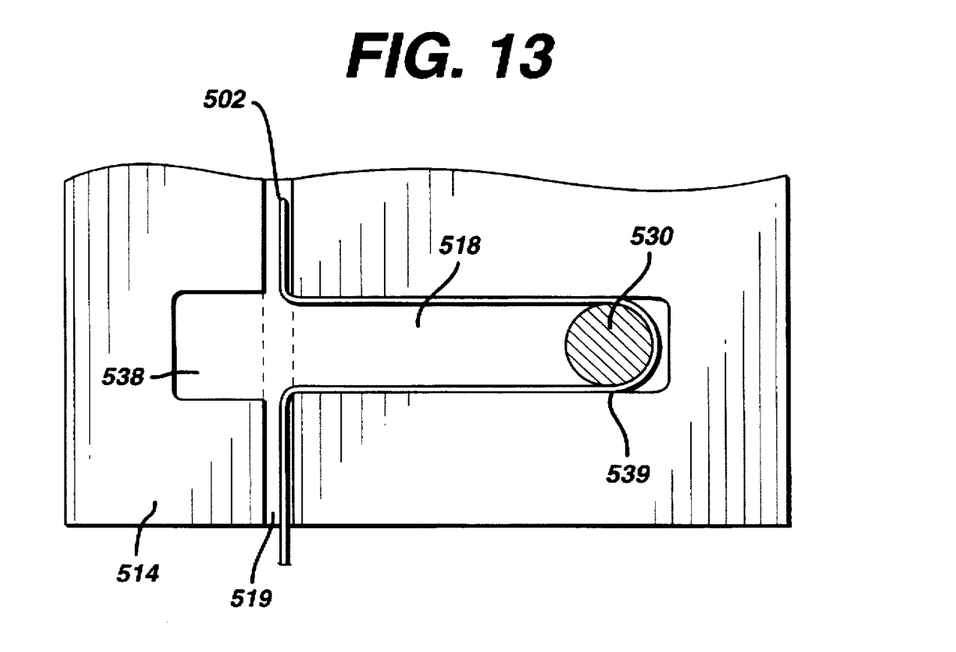

A fifth embodiment of a plug 501 according to the invention is shown in FIGS. 12 and 13.

FIG. 12 shows the rear region of the plug 501 in longitudinal section; the plug pin lies above FIG. 12. The rear region 514 of the contact piece, which is manufactured from metal, is cylindrical having a cylinder axis X—X. A recess 518 provided in the contact piece is constructed as a circular groove, see below. The rear region 514 of the contact piece also has a longitudinal channel 519 running parallel to the cylinder axis X—X, the axis of which is called Y—Y.

FIG. 13 shows the cylinder lateral area belonging to the cylinder axis X—X, which leads through the axis Y—Y, rolled into the plane of the paper. This representation illustrates the path of the recess 518 which extends as a circular groove over part of the periphery of the rear region 514 of the contact piece. The longitudinal channel 519 crosses the recess 518, i.e. the recess 518 runs at both sides of the longitudinal channel 519, wherein the arrangement in the embodiment according to FIG. 13 is asymmetric.

The rear region 514 of the contact piece is surrounded by an insulating housing 520 which is closed laterally, apart from an opening 522, see FIG. 12. The insulating housing 520 can be twisted on the rear region 514 of the contact piece. In the representation according to FIG. 12, the insulating housing 520 is rotated such that the preferably circular opening 522 is positioned over the crossing point between the recess 518 and the longitudinal channel 519. Inserted into the opening 522 is a clamping piece 530 constructed as a pin which is not shown in FIG. 12. The clamping piece 530 projects into the recess 518 and is thus guided by this circular groove.

FIG. 13 illustrates how the plug 501 is attached to a stripped wire end 502. The stripped wire end 502 is introduced into the longitudinal channel 519 from the rear plug end (i.e. in FIG. 13 from below) if the insulating housing 520 is rotated such that the clamping piece 530 is located in a starting position 538, i.e. left of the longitudinal channel 519. For clamping, the insulating housing 520 is twisted. In the process, the clamping piece 530 engages with the stripped wire piece 502 and takes it with it into the part of the recess 518 which is on the right according to FIG. 13. The stripped wire piece 502 is bent and clamped which ensures a secure mechanical seat and a good electrical contact. The end position of the clamping piece 530 which characterises the assembled state is numbered 539 in FIG. 13.

In a variant of the fifth embodiment, the insulating housing 520 is not twistable as a whole, but the clamping piece 530 is guided in a groove provided in the wall of the insulating housing 520, which groove extends along part of the periphery of the insulating housing 520 and lies over the recess 518. For this, a holding element must be provided which prevents the clamping piece 530 from dropping out of the insulating housing 520.

Shown in FIGS. 14 to 17 are other embodiments for covers which are to protect the plug pin from undesired contact.

Figure 14:
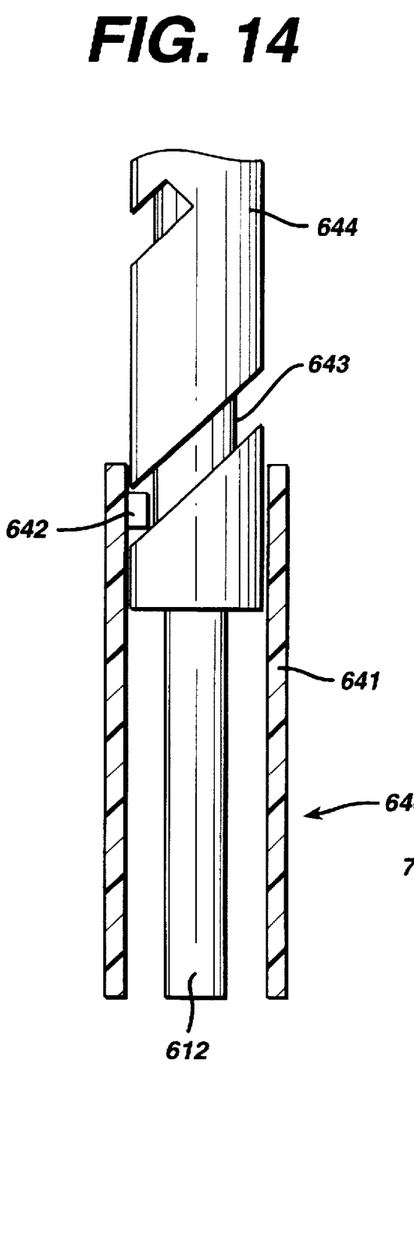

FIG. 14 shows an insulating cap 640 which is constructed as a sleeve 641. Provided in the rear edge region of its inside is a peg 642 which engages with a screw guide 643. The screw guide 643 is formed in a guide section 644 made from plastic which surrounds the rear region of the plug pin 612. In the position shown in FIG. 14 the front region of the plug pin 612 is covered by the sleeve 641. If the plug is to be inserted into a device socket or the socket of an extension lead, the sleeve 641 must firstly be screwed back.

Figure 15:
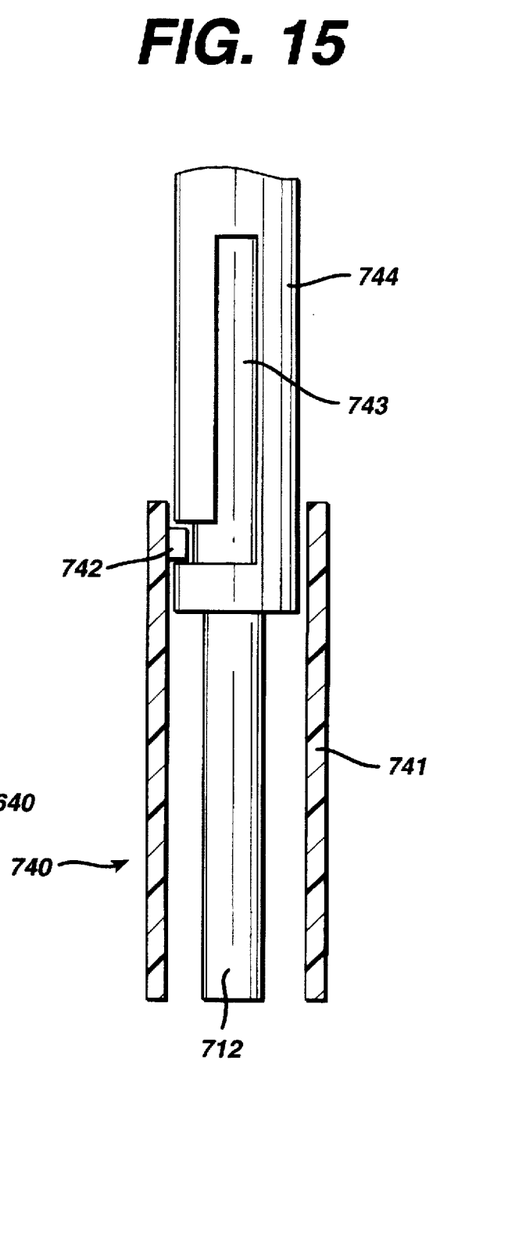

The embodiment shown in FIG. 15 is similar to that shown in FIG. 14. The plug pin 712 is surrounded by an insulating cap 740 which again is constructed as a sleeve 741 with a peg 742. However, the peg 742 glides in a bayonet guide 743 which is provided at an insulating guide section 744 which surrounds the rear end of the plug pin 712. In order to expose the front end of the plug pin 712, the sleeve 741 must be twisted and then pushed backwards.

Figure 16:
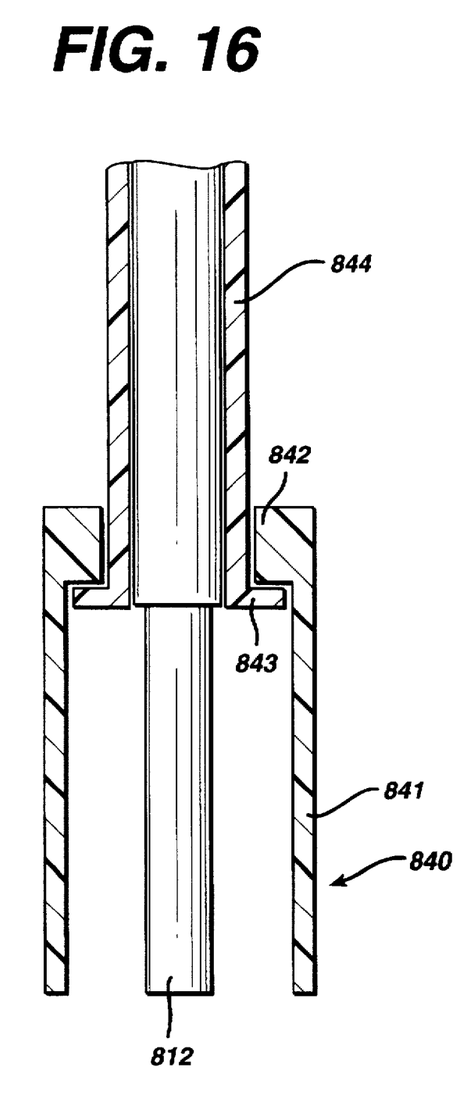

FIG. 16 shows an insulating cap 840 which is constructed as a sleeve 841 and has a circular projection 842 in the rear region. If the front region of the plug pin 812 is covered, as shown in FIG. 16, the projection 842 lies against a flange 843 which forms the front end region of a sleeve-shaped guide part 844 made from plastic which projects from the insulating housing surrounding the rear region of the contact piece.

The insulating cap 840 can be pre-tensioned by a helical spring, which is not shown in FIG. 16, which is arranged around the guide part 844 and engages with the rear face of the projection 842. Alternatively, the outside of the guide part 844 can be provided with a screw or bayonet guide with which a peg extending from the insulating cap 840 engages.

Figure 17:
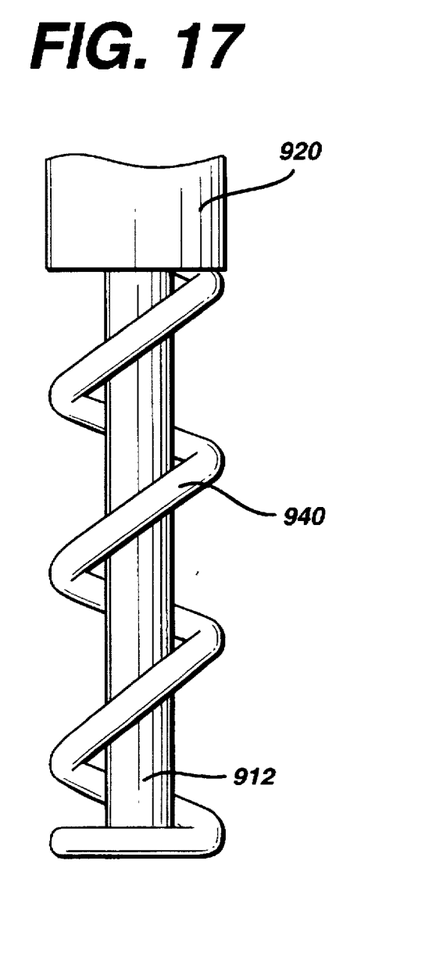

In the embodiment according to FIG. 17, the covering of the plug pin 912 is achieved, not by a closed insulating cap, but by a helical spring 940 made from insulating material. The rear end of the helical spring 940 is secured to the insulating housing 920. The helical spring 940 is pre-tensioned in such a way that, in its resting position, it surrounds the front region of the plug pin 912, as FIG. 17 shows. Upon inserting the plug, the helical spring 940 is compressed against its spring tension. Although the helical spring 940 forms no closed cover for the plug pin 912, it is still an effective contact protection. It can be made from plastic or also be a steel spring sheathed by a plastic jacket.

In a preferred variant, which is not shown in the figures, the front region of the plug pin is surrounded by an insulating bellows which is secured in the rear region of the plug pin. Upon inserting into a socket, the bellows is compressed. In order to ensure that the plug pin is automatically shielded when the plug is pulled out, the bellows can be placed under a suitable pre-tension or be extended by an additional spring.

What is claimed is:

1. A plug for connection to the stripped end (102; 202; 302; 402; 502) of a heart electrode wire or of another implantable wire, having a contact piece (110; 210, 310), the front region of which is constructed as a plug pin (112; 212; 312) and the rear region (114; 214; 314; 414; 514) of which has a recess (118; 218; 318; 418, 518), an insulating housing (120; 220; 320; 420; 520) which surrounds the rear region (114; 214; 314; 414; 514) of the contact piece and leaves free access to the recess (118; 218; 318; 418; 518);

a clamping piece (130; 230; 330; 430; 530), which in the assembled state engages with the recess (118; 218; 318; 418; 518), whereby the stripped wire end (102; 202; 302; 402; 502) is bent round and clamped in the recess (118; 218; 318; 418; 518) wherein the recess (118) runs in the direction of the longitudinal axis (L—L) of the plug (101) and is accessible from the rear end of the contact piece (110) wherein the clamping piece (130) is provided with a transverse bore (133) to guide through the stripped wire end (102), wherein the clamping piece (130; 230; 330; 430; 530) consists completely of insulating material; and wherein the recess (118) is cylindrical and the clamping piece (130) essentially fills the recess (118) in the assembled state, the diameter of the front end region (131) of the clamping piece (130) being matched to the inside diameter of the recess (118), the clamping piece (130) having a smaller diameter in the middle region (132) in which the through bore (133) is arranged and the rear end region (134; 135) of the clamping piece (130), which projects from the recess (118) in the assembled state, being wider to cover the rear end of the contact piece (110), wherein the recess (218; 318; 418; 518) is arranged laterally at the contact piece (210; 310), wherein the recess (218; 318) is accessible via a longitudinal groove (224; 324), arranged laterally at the insulating housing (220; 320), wherein the clamping piece (230) is provided with stop elements (236) which engage with corresponding counterparts (228) at the insulating housing (220) in the assembled state, wherein the clamping piece (330) has a wall section (333) which, in the assembled state, covers the rear end of the longitudinal groove (324), wherein the clamping piece (230) can be pushed laterally onto the insulating housing (220), wherein the clamping piece (330) is constructed as one piece with the insulating housing (320) and can be hinged about a film hinge (337) for assembly, wherein in the non-assembled state, the stripped wire end (402) can be introduced from the rear end into the plug (401) via a longitudinal channel (419) cutting or crossing the recess (418), in that the insulating housing (420) is closed laterally apart from an opening (422) over the recess (418), and in that the clamping piece (430) is formed as a pin (432; 434) which can be pushed laterally into the opening (422) and the recess (418), wherein the recess (518) is constructed as a circular groove which extends along part of the periphery of the rear region (514) of the contact piece, in that the stripped wire end (502) can be introduced into the plug (501) in the non-assembled state, from the rear end via a longitudinal channel (519) in the contact piece, which channel crosses the recess (518), in that the insulating housing (520) can be twisted on the rear region (514) of the contact piece and in that the clamping piece (530) is formed as a pin guided in the circular groove (518).

2. The plug according to claim 1, characterized in that plug pin (912) is surrounded by a helical spring (940), attached in its rear region, made from insulating material, which can be compressed against its spring tension, exposing the front region of the plug pin (912).

3. The plug according to claim 1, characterized that an insulating cap (140; 240; 340; 640; 740; 840) is provided to cover the plug pin (112; 212; 312; 612; 712; 812).

4. The plug according to claim 3, characterized in that the insulating cap (640; 740; 840) is constructed as a sleeve (641; 741; 841) which, in the insulating state, surrounds the front region of the plug pin (612; 712; 812) and can be moved backwards on an insulating guide (644; 744; 844) arranged around the rear region of the plug pin (612; 712; 812).

5. The plug according to claim 3, characterized in that the insulating cap is constructed as an insulating bellows which is attached in its rear region.

6. The plug according to claim 3, characterized in that the insulating cap (140) is constructed as a sleeve (141) which, in an insulating state, surrounds the front region of the plug pin (112) and can be moved backwards into an insulating intermediate housing (144) arranged around the rear region of the plug pin (112).

7. The plug according to claim 6, characterized in that the sleeve (141) can be moved backwards against the force of a spring (148).

8. The plug according to claim 6, characterized in that the sleeve (641; 741) is guided by means of a screw guide (643) or a bayonet guide (743) at the intermediate housing or the insulating guide (644; 744).

* * * * *